(12) United States Patent
Harnoncourt et al.

(10) Patent No.: US 7,635,339 B2
(45) Date of Patent: Dec. 22, 2009

(54) METHOD FOR NON-COOPERATIVE LUNG FUNCTION DIAGNOSIS USING ULTRASOUND

(75) Inventors: Karl Harnoncourt, Graz (AT); Christian Buess, Horgen (CH)

(73) Assignee: ndd Medizintechnik AG, Zurich (CH)

( * ) Notice: Subject to any disclaimer, the term of this patent is extended or adjusted under 35 U.S.C. 154(b) by 548 days.

(21) Appl. No.: 11/219,457

(22) Filed: Sep. 2, 2005

(65) Prior Publication Data

US 2007/0191726 A1     Aug. 16, 2007

Related U.S. Application Data

(60) Provisional application No. 60/606,963, filed on Sep. 3, 2004.

(51) Int. Cl.
    *A61B 5/08*     (2006.01)
(52) U.S. Cl. ...................... 600/532; 600/529
(58) Field of Classification Search ............... 600/532
    See application file for complete search history.

(56) References Cited

U.S. PATENT DOCUMENTS

| | | | |
|---|---|---|---|
| 3,896,792 A | 7/1975 | Vail et al. | |
| 5,419,326 A | 5/1995 | Harnoncourt | |
| 5,503,151 A * | 4/1996 | Harnoncourt et al. | 600/438 |
| 5,645,071 A * | 7/1997 | Harnoncourt et al. | 600/532 |
| 6,629,934 B2 * | 10/2003 | Mault et al. | 600/538 |
| 6,817,250 B2 * | 11/2004 | Cardelius et al. | 73/861.27 |
| 7,108,659 B2 * | 9/2006 | Ross et al. | 600/529 |
| 7,127,936 B2 * | 10/2006 | Cardelius et al. | 73/24.01 |
| 7,152,490 B1 * | 12/2006 | Freund et al. | 73/861.27 |
| 7,445,601 B2 * | 11/2008 | Kline | 600/532 |
| 2001/0029340 A1 | 10/2001 | Mault et al. | |
| 2003/0023181 A1 * | 1/2003 | Mault | 600/532 |
| 2003/0208133 A1 * | 11/2003 | Mault | 600/532 |
| 2004/0093957 A1 * | 5/2004 | Buess et al. | 73/861.27 |
| 2008/0031507 A1 * | 2/2008 | Uppaluri et al. | 382/132 |

FOREIGN PATENT DOCUMENTS

| | | |
|---|---|---|
| CH | 669463 | 3/1989 |
| EP | 0597060 | 4/1997 |
| EP | 0653919 | 9/2001 |
| EP | 1279368 | 1/2003 |
| WO | 00/28881 | 5/2000 |
| WO | 02/17991 | 3/2002 |

OTHER PUBLICATIONS

Buess et al., "Design and Construction of a Pulsed Ultrasonic Air Flow Meter," IEEE Trans Biomed. Eng. 33 (8): 768-774, Aug. 1986.
Buess et al., "Ultrasonic Respiration Analysis," IEEE/EMBS 13$^{th}$ Annual Conference, pp. 1597-1598, Orlando, U.S.A. Nov. 1991.
You et al. "Expiratory Capnography in Asthma : Evaluation of Various Shape Indices," Eur Respir J. 1994, 7, pp. 318- 323.
Krauss et al., "Capnogram Shape in Obstructive Lung Disease," Anesth. Analg. 2005, 100:884-888.

* cited by examiner

*Primary Examiner*—Patricia Mallari
*Assistant Examiner*—Karen E Toth
(74) *Attorney, Agent, or Firm*—Dilworth & Barrese, LLP

(57) ABSTRACT

A method and device are provided for measuring state of lung function of a patient using ultrasonic flow and molar mass measurement. Flow and molar mass signals are recorded during tidal breathing without requiring patient cooperation. Statistical analysis of the recorded data in combination with anthropometirc data and/or data form a questionnaire can be used to diagnose various pulmonary ailments or diseases.

14 Claims, 7 Drawing Sheets

मेथड FOR NON-COOPERATIVE LUNG FUNCTION DIAGNOSIS USING ULTRASOUND

METHOD FOR NON-COOPERATIVE LUNG FUNCTION DIAGNOSIS USING ULTRASOUND

CROSS-REFERENCE TO RELATED APPLICATIONS

The present application claims priority under 35 U.S.C. § 119(e) to co-pending provisional application Ser. No. 60/606,963 filed Sep. 3, 2004.

BACKGROUND OF THE INVENTION

1. Field of the Invention

The present disclosure relates generally to a device and method for lung function diagnosis, and more particularly to a device and method for non-cooperative lung function analysis using flow and molar mass data from ultrasonic transit time measurements during quiet breathing with a portable spirometer.

2. Description of Prior Art

There are several systems described for lung function diagnosis based on the analysis of flow (and therefore volume, determined by integration of the flow) combined with a gas analysis signal, e.g., You et al. "Expiratory Capnography in Asthma: Evaluation of Various Shape Indices" (*Eur Respir J.*, 7; 318-323, 1994) and Krauss et al. "Capnogram Shape in Obstructive Lung Disease" (*Anesth Analg*, 100:884888, 2005). All systems use separate gas analysis devices for measuring the $CO_2$ concentration, e.g. mass spectrometers or devices based on infrared absorption. In some cases defined breathing maneuvers are used.

Generally, most of the lung function tests in primary care are performed by executing so-called "forced" expiratory maneuvers. During such a test, a patient must fully inhale and then perform a sudden, forced expiration until no more gas can be exhaled. The test may be followed by a forced inspiratory maneuver. Analysis of the flow over a volume graph and/or volume over a time graph results in a set of parameters that are used for lung function diagnosis. To perform such a test, the procedure must be explained to the patient in detail and the patient must follow the guidelines of the test with great care. Generally, the tests must be repeated at least three times to obtain a measure of sufficient test quality. The tests are relatively difficult to explain and also exhausting for the patient. Furthermore, the test can only be performed successfully if the technician performing the test is well trained.

Many other medical tests that are used for screening, for example, measuring of blood pressure or electrocardiogram (ECG), do not require this type of patient cooperation.

Accordingly, it is an object to improve pulmonary diagnostic testing and analysis.

It is a more specific object of the present invention to improve such pulmonary diagnostic testing and analysis minimizing discomfort of a patient being tested.

It is a further object of the present invention to expedite and simplify pulmonary diagnostic testing and analysis.

It is a further more specific object of the present invention to both improve ease of the pulmonary diagnostic testing and analysis for an administering technician or medical personnel and at the same time minimize instructions to a patient being tested.

It is another object of the present invention to provide effective pulmonary diagnostic testing and analysis of a patient without need for the patient's active intervention, e.g., while the patient might be unconscious or otherwise unable to cooperate.

SUMMARY OF THE INVENTION

These and other objects are explicitly attained by the present invention which is directed to a device comprising an ultrasonic gas flow and molar mass sensor for medical application and based upon a transit-time or time-of-flight procedure, an exchangeable or fixed flow tube having a mouthpiece, and appropriate software for non-cooperative tidal breathing analysis of patients by measuring flow, volume and molar mass, using statistical methods for analysis of resulting signals, and subsequently deriving, from the analysis results, lung function status index for diagnostic or monitoring purposes.

The present invention is based upon an inexpensive, simple to use device and method solely based, in turn, on an ultrasonic flow and molar mass sensor. Attention or cooperation by the patient with the measuring procedure is not required. The device and method of the present invention measure state of lung function of a patient using ultrasonic flow and molar mass measurement. Flow and molar mass signals are recorded during tidal breathing and require no patient cooperation. Statistical analysis of the recorded data in combination with anthropometric data and/or data from a questionnaire may be used to diagnose Chronic Obstructed Pulmonary Disease (COPD), asthma or other respiratory diseases.

BRIEF DESCRIPTION OF THE DRAWINGS

The above and other objects, features and advantages of the present invention will become more apparent from the following detailed description when taken in conjunction with the accompanying drawings in which.

DESCRIPTION OF THE PREFERRED EMBODIMENT

A preferred embodiment of the present invention will be described hereinbelow with reference to the accompanying drawings. In the following description, well-known functions or constructions are not described in detail since they are clearly understood in the art upon consideration of the present disclosure.

The present invention is directed to a method for non-cooperative lung function analysis using flow and molar mass data from an ultrasonic transit-time or time-of-flight flow meter. The operation of an ultrasonic flow meter is disclosed in, for example, European Patent Nos. 0597060 B1; 0653919 B1; Buess et al. "Design and Construction of a Pulsed Ultrasonic Air Flowmeter" (IEEE Trans. Biomed. Eng., 33(8):768-774, August, 1986); Buess et al. "Ultrasonic Respiration Analysis" (IEEE/EMBS 13th Annual Conference, 1597-1598, Orlando, USA, November, 1991); and U.S. Pat. Nos. 5,419,326 issued May 30, 1995 and U.S. Pat. No. 5,645,071 issued Jul. 8, 1997. The entire contents of all six of these citations are incorporated by reference herein. The method according to the present invention can also easily be integrated into a hand held device or in a simple device connected to a computer. Testing is easy to perform and does not require trained technicians.

Figure 1:
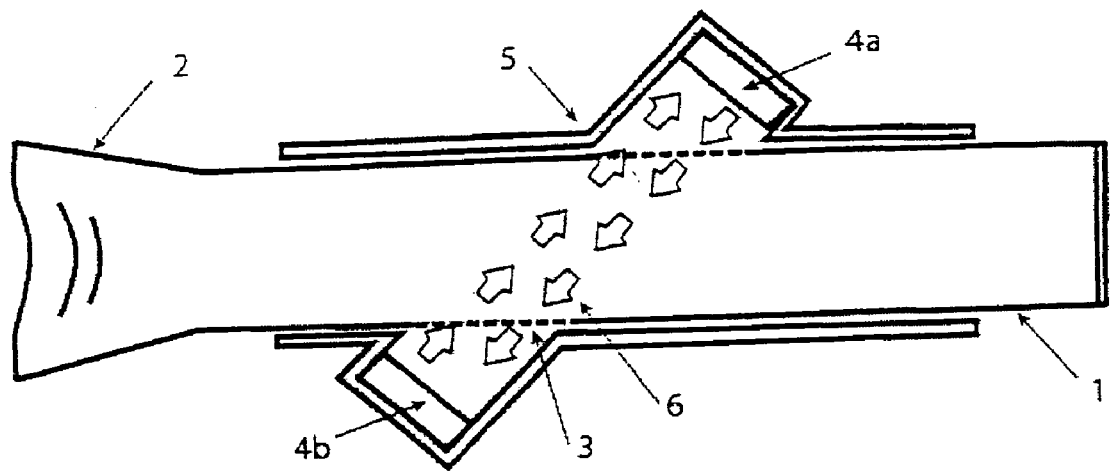
FIG. 1 illustrates a cross-sectional view of an ultrasonic flow meter according to an embodiment of the present invention.
Figure 2:
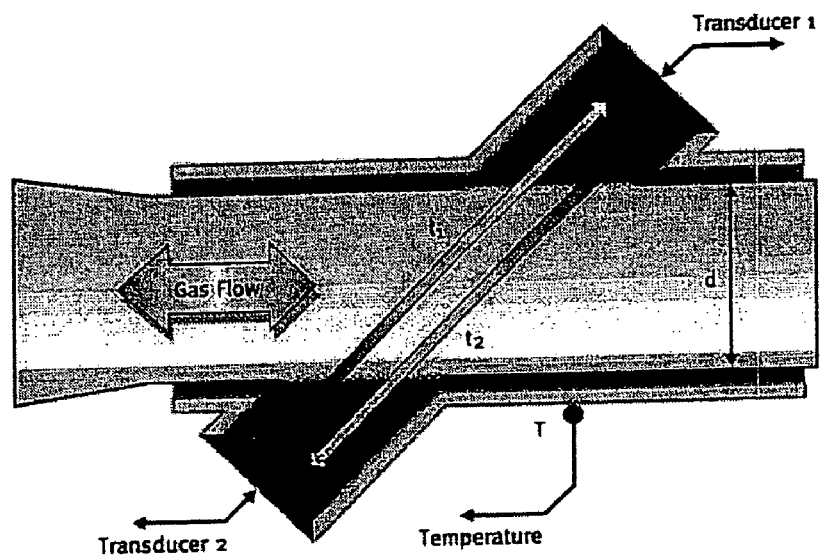
FIG. 2 illustrates a schematic view, similar to FIG. 1, of an ultrasonic flow meter showing transit time differences between upstream and downstream ultrasound pulses according to an embodiment of the present invention.

FIGS. 1 and 2 illustrates a cross-sectional view of an ultrasonic flow meter showing the operation principle according to the present invention. Referring to FIG. 1, the device of the present invention comprises two ultrasonic transducers 4a, 4b mounted on opposite sides of the gas flow, an encompassing case 5 securing the transducers 4a, 4b, an exchangeable breathing tube 1 and a mouthpiece 2 attached to the flow tube 1. The flow velocity is determined using the transit-times (time-of-flight) of pulse trains 6 in upstream and downstream direction of the gas flow. The pulse trains 6 are transmitted and received by the ultrasonic transducers 4a, 4b and pass through the exchangeable flow tube 1 through ultrasonically permeable parts 3 of the flow tube 1, such as meshes or filters.

Referring to FIG. 2, transit time differences, e.g., $t_1-t_2$, between upstream and downstream ultrasound pluses are used to measure gas flow velocity. The bigger the difference in transit time $t_1-t_2$, the faster the velocity (cm/sec). The flow velocity (cm/sec) multiplied by cross-sectional area of the tube 1 (cm$^2$) gives flow (cm$^3$/sec or ml/sec). Finally, flow is integrated to obtain volume measures. Flow velocity is determined using the following equation (1):

$$F = k_1 \frac{t_1 - t_2}{t_1 \cdot t_2} \quad (1)$$

where F is the velocity of the gas flow, $t_1$ and $t_2$ represent the transit-times in upstream and downstream direction, and k, is a mechanical constant. Alternatively, a simplified equation as described in Buess et al., (IEEE Trans. Biomed. Eng., 33(8): 768-774, August, 1986) may be used.

Molar mass is determined using the following equation (2):

$$M = k_2 \cdot T \cdot \frac{(t_1 \cdot t_2)^2}{(t_1 + t_2)^2} \quad (2)$$

where M is the molar mass, T is the mean temperature along the sound transmission path, $t_1$ and $t_2$ represent the transit-times and $k_2$ is a constant, which is described in European Pat. No. 0653919 B1 and U.S. Pat. No. 5,645,071.

Since measurement of the mean temperature along the sound transmission path is difficult, it is distinguished with "normal" molar mass and "native" molar mass. Normal molar mass approximates the temperature along the sound transmission path by determining the mean temperature along the sound transmission path using one or several temperature measurements in combination with appropriate mathematical models, which is described in European Pat. No. 0653919 B1 and U.S. Pat. No. 5,465,071. Native molar mass, on the other hand, is determined using a fixed temperature of e.g. zero degrees Celsius. Native molar mass is therefore a mixed gas composition and temperature measurement of the gas flow.

In contrast to other methods using flow- and gas composition (or gas concentration) measurement, the ultrasonic transit-time analysis determines the overall molar mass of the gas mixture and not the concentration of a specific gas. Since flow and molar mass signals, however, are always time aligned, there is no delay between flow and molar mass signals. For most other gas analysis methods this is not the case, and algorithms for time alignment between flow and gas signals must be used to perform analysis of gas concentration versus flow or volume signals.

As pointed out above, the present invention is based on an inexpensive, simple to use device that is solely based on an ultrasonic flow and molar mass sensor. The measurement is performed using tidal breathing analysis. Tidal breathing is recorded over a period of 30 seconds up to several minutes. The measurement is therefore a non-cooperative measurement that requires neither attention nor cooperation by the patient.

Figure 3:
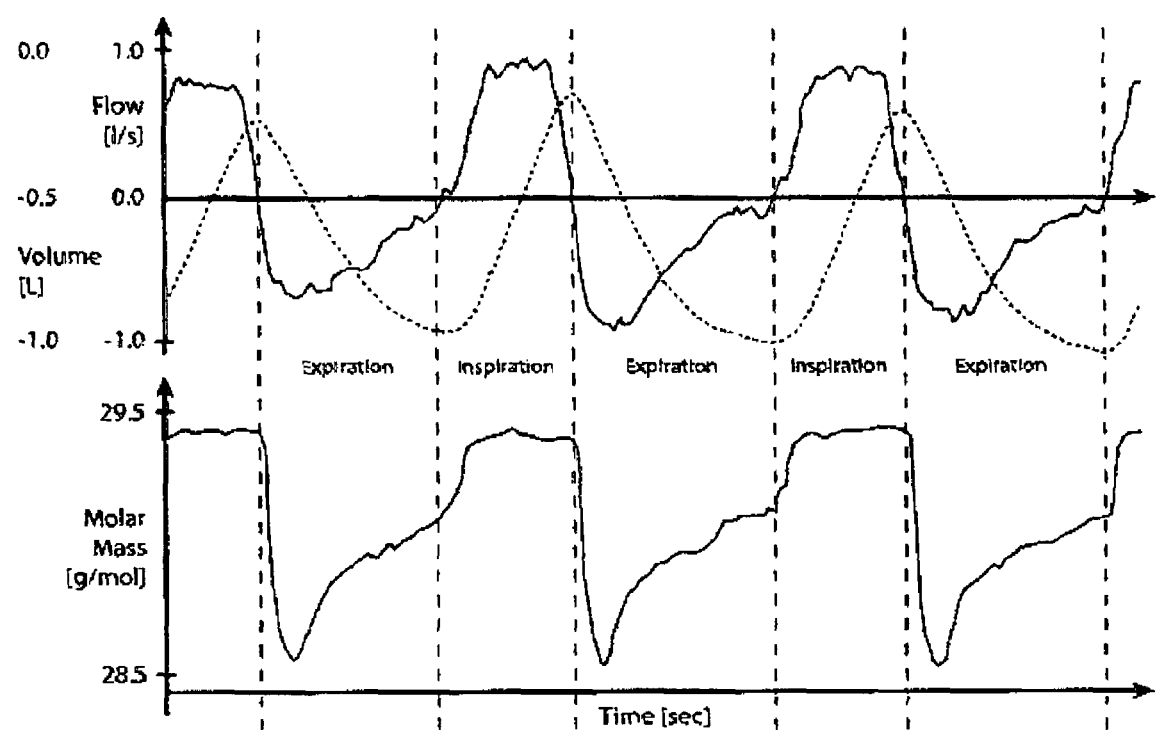
FIG. 3 illustrates a graph showing molar mass, flow and volume changes over time during quiet breathing according to an embodiment of the present invention.
Figure 4:
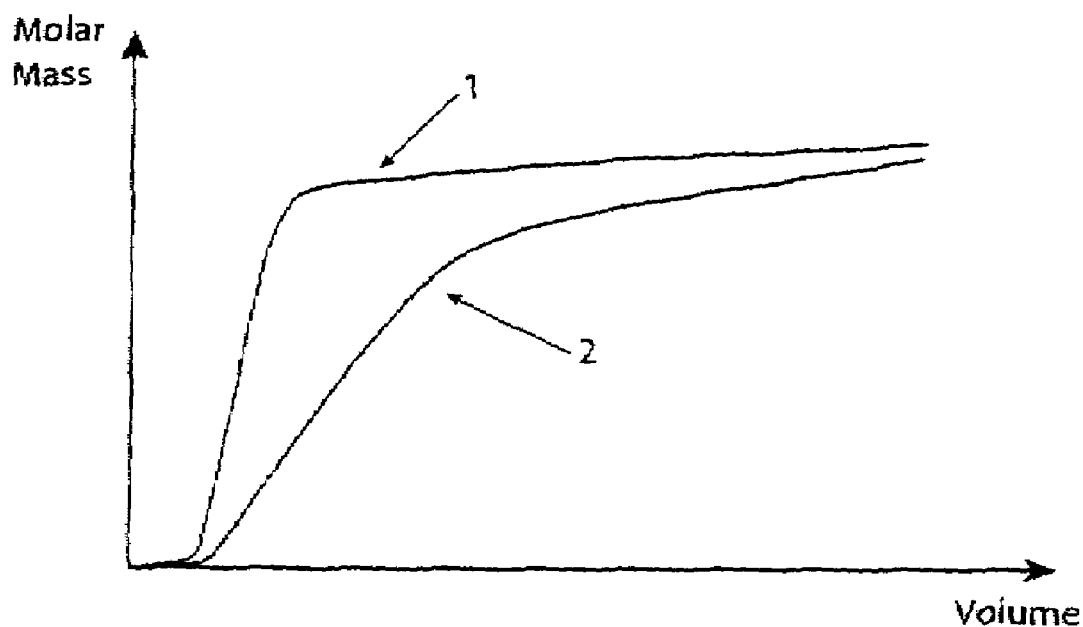
FIG. 4 illustrates a graph showing molar mass over volume of two patients with different lung function status according to an embodiment of the present invention.

The signals of flow, volume (e.g., integrated flow) and molar mass are used for the subsequent data analysis. FIG. 3 illustrates the molar mass, flow and volume changes over time during quiet breathing. As explained above, native molar mass or normal molar mass is used for the analysis. Molar mass is plotted over volume or time and a shape analysis is performed. FIG. 4 illustrates the molar mass over volume graph of two patients with different lung function status; curve 1 represents a healthy patient while curve 2 represents a patient with a pulmonary disease, e.g., chronic obstructive pulmonary disease (COPD) or asthma.

Figure 5:
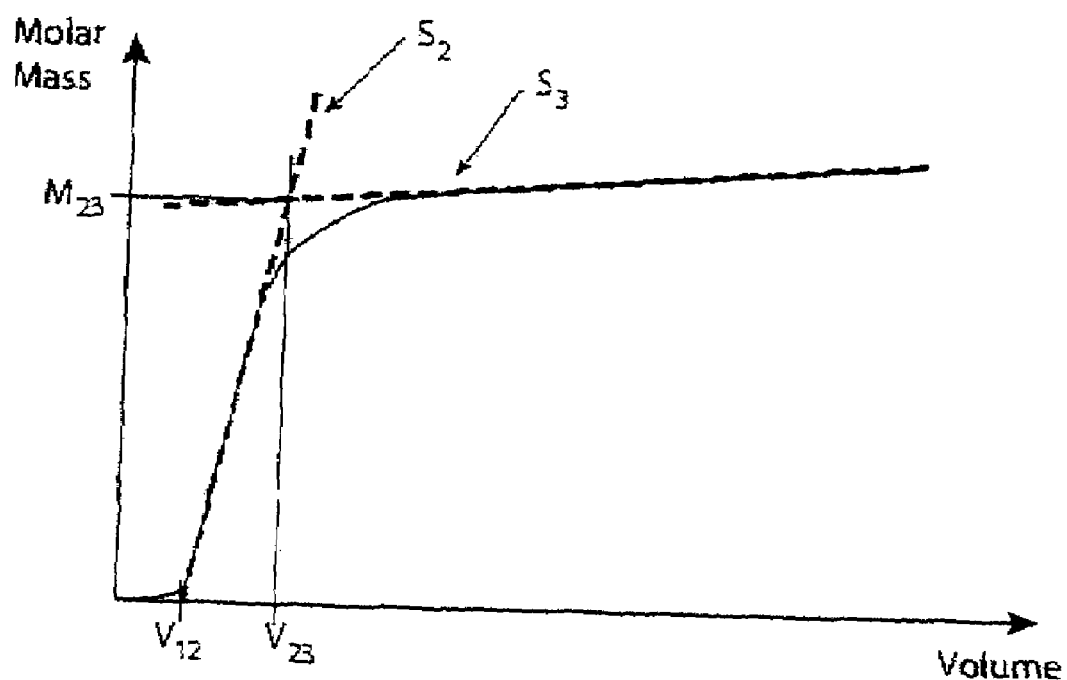
FIG. 5 illustrates a graph showing molar mass over volume with regression lines (e.g., slopes, x-intercepts) according to an embodiment of the present invention.
Figure 6:
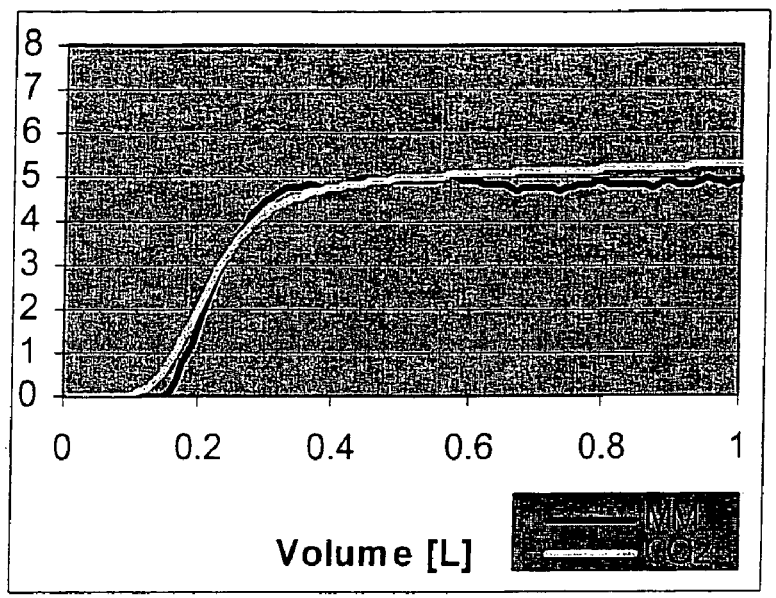
FIG. 6 illustrates a graph showing molar mass over volume of a normal breathing pattern according to an embodiment of the present invention.
Figure 7:
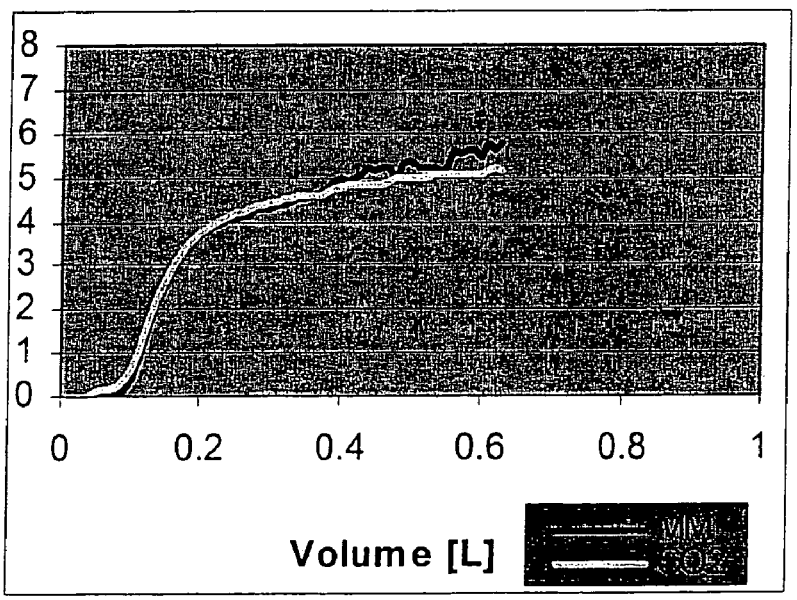
FIG. 7 illustrates a graph showing molar mass over volume of a mildly obstructed breathing pattern according to an embodiment of the present invention.
Figure 8:
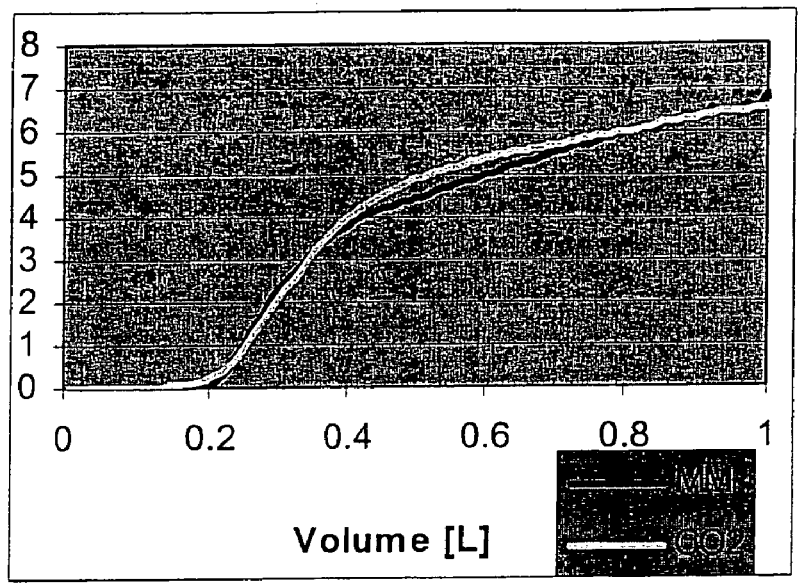
FIG. 8 illustrates a graph showing molar mass over volume of a moderately obstructed breathing pattern according to an embodiment of the present invention.
Figure 9:
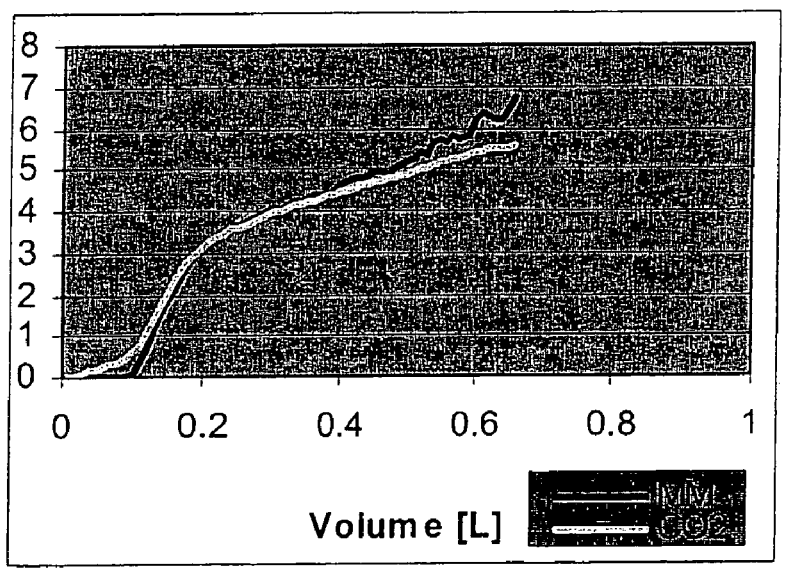
FIG. 9 illustrates a graph showing molar mass over volume of a severely obstructed breathing pattern according to an embodiment of the present invention.

To compute a lung function status index for diagnosis of COPD, asthma or other pulmonary diseases, statistical methods based on flow (i.e., volume), time and molar mass are used. The statistical analysis used for predicting lung function status is solely based on the shape of molar mass over volume (or time) graph; it can also be based on a combination of molar mass shape analysis with other parameters, e.g., derived from the flow pattern during quiet breathing. FIG. 5 illustrates an example where the shape analysis is performed by using two regression lines. The shape analysis can be based on the mathematical parameters that define the regression lines (e.g. slopes, X-intercepts) and the intersection between the two regression lines.

The statistical analysis used for prediction can use techniques such as "fuzzy class" prediction. In addition, the statistical analysis may include anthropometric data from the patient and/or data from a questionnaire answered by the patient. Furthermore, the molar mass over volume, flow, or time analysis uses a single breath selected randomly or selection criteria for the breath cycle that is considered for data analysis. The analysis also uses an overlay technique where several breaths are overlaid to form a mean shape. The above-described method can be implemented in a standalone device, e.g., a hand-held ultrasonic spirometer, or alternatively a computer-based device where an ultrasonic flow and molar mass sensor is interfaced to a computer that is used for data analysis and representation.

Hereinafter, the present invention will be described in detail by way of the following examples, which are not intended to limit the scope of the present invention.

EXAMPLE 1

Patients with airway obstruction can be identified and categorized as to severity with measures of $CO_2$ and spirometric flow patterns during quiet breathing. Sixty five healthy subjects and patients (35 men, 30 women) with mean age of 48.4 were tested in the pulmonary laboratory. They breathed quietly for 5 minutes on an ndd ultrasonic spirometer (ndd, Zurich, Switzerland) while seated using nose clips. Standard spirometry was conducted on all subjects, except one, prior to performing the quiet breathing on the ultrasonic molar mass device. PFT measurements of FVC and FEV1 and percent predicted values (using NHANES III reference equations) were obtained and used to categorize the subjects into normal, mild, moderate or severe obstruction or restricted. Diffusion capacity (DLCO) was measured only in scheduled patients.

Molar Mass (MM) measurement is a potential surrogate for $CO_2$ measurement in pulmonary function testing. Molar mass measurements were compared to $CO_2$ measurements made with a mass spectrometer. The sensor can simultaneously measure the molar mass of the exhaled gas using the same transit time signals used to measure air flow. $CO_2$ was simultaneously measured with a mass spectrometer (mspec) which was calibrated prior to each test and estimated with molar mass (MM) determined from the ndd spirometer.

Composite capnograms (% $CO_2$mspec vs. volume and % $CO_2$MM vs. volume) were created for each subject by averaging the % $CO_2$mspec concentrations at matched exhalation volumes. Maximum slope and the volume where the maximum slope occurred were calculated from the composite curves for each subject. In addition, slope of phase III was calculated. Linear discriminant analysis was used to compare percentage of correct classifications using $CO_2$mspec data and the $CO_2$MM data. Additional analyses were performed using only the molar mass data and adding age and gender to the discriminant analysis. A final classification analysis was performed categorizing subset only into "normal" or "any obstruction" using the molar mass data.

The speed of sound in a gas is proportional to the molar mass of a gas mixture. Although the temperature alters the speed of sound within the gas mixture, it can be compensated for in the calculations. Mean molar mass of a mixture of n gases is determined as:

$$\text{Sum}_{(i=1 \ to \ n)}[\text{molecular weight}_{[gas(i)]} \times \text{Concentration}_{[gas(i)]}]$$

Molar mass is directly measured from the average sound velocity. Accuracy of molar mass measurements is 0.034%. Table 1 illustrates an example of molar mass for room air and end tidal gas from the lungs.

TABLE 1

| Gas | Concentration | Molar Weight (g/mol) | Fractional Molar Mass (g/mol) |
|---|---|---|---|
| Room Air | | | |
| Nitrogen | 0.7810 | 28 | 21.8680 |
| Oxygen | 0.2093 | 31.99 | 6.6955 |

TABLE 1-continued

| Gas | Concentration | Molar Weight (g/mol) | Fractional Molar Mass (g/mol) |
|---|---|---|---|
| Carbon Dioxide | 0.0003 | 44 | 0.0132 |
| Argon | 0.0094 | 39.95 | 0.3755 |
| | 1 | | |
| Mean Molar mass of air at 0% humidity | | | 28.95 |
| End Tidal Gas From the Lungs | | | |
| Nitrogen | 0.77998 | 28 | 21.8364 |
| Oxygen | 0.14 | 31.99 | 4.4786 |
| Carbon Dioxide | 0.07 | 44 | 3.0800 |
| Argon | 0.0094 | 39.95 | 0.3755 |
| Water | 0.00062 | 18 | 0.0112 |
| | 1 | | |
| Mean Molar mass of end tidal gas | | | 29.78 |

Figure 10:
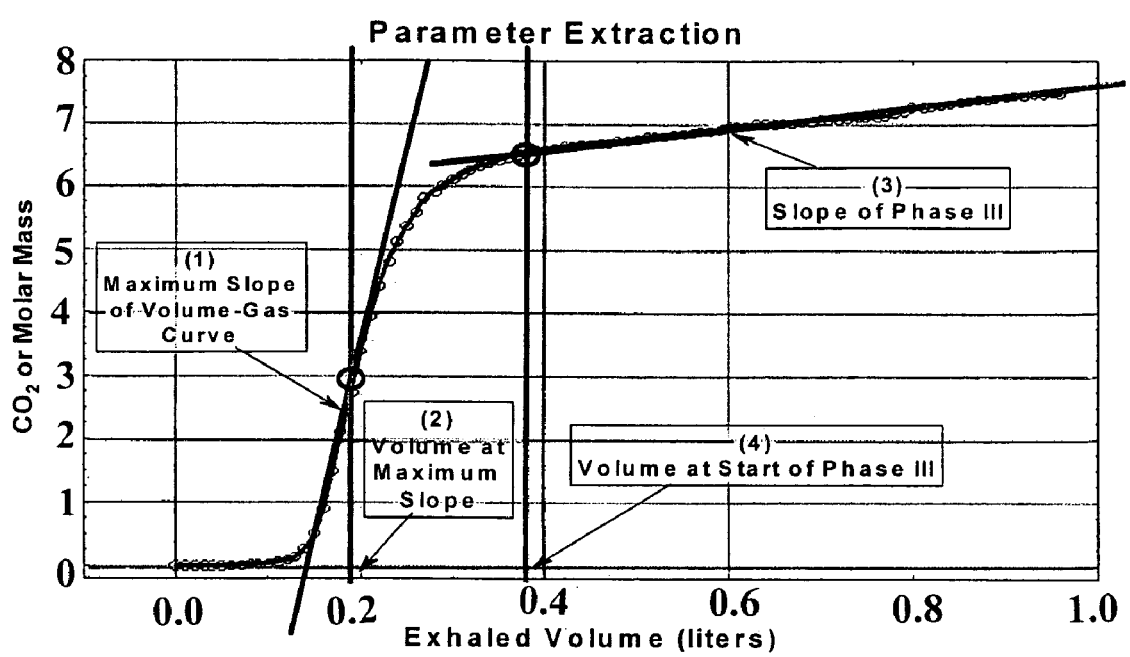
FIG. 10 illustrates a graph showing parameters extracted from composite curves according to an embodiment of the present invention.

Parameters such as P1, P2, P3, P4 are extracted from composite curves. P1 indicates maximum slope of the volume-gas curve; P2 indicates volume where the maximum slope occurs; P3 indicates slope of phase III of the volume-gas curve; P4 indicates volume at beginning of Phase III. Referring to FIG. 10, each of the parameters are calculated from the composite curve.

FVC, FEV1, PEF and FEV1/FVC ratio was measured with the spirometer. Average values for FEV1 and FEV1/FVC in each disease category are listed in Table 2, along with mean parameter values. There is excellent correlation between the parameters, P1, P2, P3 and P4, derived from the mass spectrometer measured % $CO_2$ vs. volume curves and the ultrasonic measured molar mass vs. volume curves (correlations for P1: $r^2=0.909$, P2: $r^2=0.961$, P3: $r^2=0.729$, P4: $r^2=0.960$).

TABLE 2

| | Normal | Mild | Moderate | Severe |
|---|---|---|---|---|
| FEV1 (L) | 3.39 | 2.45 | 1.65 | 1.47 |
| FEV1/FVC (%) | 79.2 | 62.3 | 51.5 | 44.4 |
| MAX Δ % $CO_2$/L | 55.2 | 42.4 | 44.3 | 35.4 |
| Volume at Max Δ % $CO_2$/L | 0.122 | 0.162 | 0.123 | 0.142 |
| Slope phase III | 1.97 | 3.95 | 4.73 | 4.49 |
| Volume at phase III | 0.174 | 0.225 | 0.176 | 0.197 |

The information contained in the molar mass derived parameters can correctly categorize 79% of pulmonary patients. When age and gender are added to the discriminant analysis 82% of the patients were correctly classified.

Table 3 illustrates the separate discriminant analyses using only $CO_2$ measurements from mass spectrometer. Almost 80% of the patients were separated into normal or disease. Overall, no difference was found between the mass spectrometer % $CO_2$ vs. volume parameters and the molar mass vs. volume parameters to correctly classify patients into the simple "normal" or "any obstruction" groups. The MM parameters were more consistent in their classifications.

TABLE 3

|  | % correctly classified with mass spec % $CO_2$ | % correctly classified with molar mass |
| --- | --- | --- |
| Spirometry: Normal | 68.8 | 78.1 |
| Spirometry: Any obstruction | 90.0 | 80.0 |
| Overall: Correctly classified | 79.0 | 79.0 |

Classifying patients into their correct level of obstruction was less accurate. For % $CO_2$ and molar mass, about 60% of the patients were classified into their correct obstructed level (mild, moderate or severe) or normal groups. There were only three restricted patients and the discriminant analysis generally categorized these into a normal pattern.

Thus, it can be concluded molar mass measurements are sampled and correlate well with traditional $CO_2$ measurements and can provide an independent test which will diagnose both presence and degree of airway obstruction.

EXAMPLE 2

Patients with airway obstruction can be identified and categorized as to severity with measures of $CO_2$ and spirometric flow patterns during quiet breathing. Molar mass measures were compared to $CO_2$ measurements made with a mass spectrometer. Thirty six individuals were tested in the pulmonary laboratory. Clinical classifications from spirometry, DLCO and physician diagnosis is carried out on sixteen healthy subjects, four patients with mild obstruction, six patients with moderate obstruction and ten patients with severe obstruction.

Average values for FEV1 and FEV1/FVC in each disease category are listed in Table 4, along with mean parameter values. There is excellent correlation between the parameters (1-4) derived from the mass spectrometer measured % $CO_2$ vs. volume curves and the ultrasonic measured molar mass vs. volume curves.

TABLE 4

|  | Normal | Mild | Moderate | Severe |
| --- | --- | --- | --- | --- |
| FEV1 (L) | 3.11 ± 0.75 | 3.24 ± 0.84 | 1.91 ± 0.74 | 1.55 ± 0.55 |
| FVC/FEV1 (%) | 77.9 ± 8.6 | 66.3 ± 3.0 | 59.3 ± 6.6 | 46.4 ± 8.9 |
| MAX Δ % $CO_2$/L | 3.54 ± 1.80 | 2.82 ± 1.36 | 3.37 ± 1.62 | 1.75 ± 0.48 |
| Volume at Max Δ % $CO_2$/L | 0.120 ± 0.031 | 0.172 ± 0.062 | 0.123 ± 0.021 | 0.141 ± 0.036 |
| Slope phase III | 2.19 ± 1.45 | 4.82 ± 1.85 | 4.74 ± 3.33 | 4.90 ± 2.23 |
| Volume at phase III | 0.450± | 0.443 ± 0.015 | 0.435 ± 0.037 | 0.450± |

The % $CO_2$MM measurements accurately tracked the % $CO_2$mspec data which correctly categorized 72% of the subjects into their spirometric "normal" or "obstruction" category. Molar mass data correctly categorized 67% of the subjects. Adding age and gender, the molar data correctly categorized 78% and finally molar mass data correctly classified 83% into either "normal" or "any obstruction."

Molar mass signals to $CO_2$ signals measured simultaneously with a mass spectrometer were compared in FIGS. 6-9, which show similar patterns for both $CO_2$ and molar mass signals. Volume/time, % $CO_2$mspec and % $CO_2$MM were sampled at 200 Hz throughout each respiratory cycle using ultrasonic flow sensor. % $CO_2$MM/volume graphs for normal, mild obstruction, moderate obstruction and severe obstruction patterns are illustrated in FIGS. 6-9 respectively.

Figure 11:
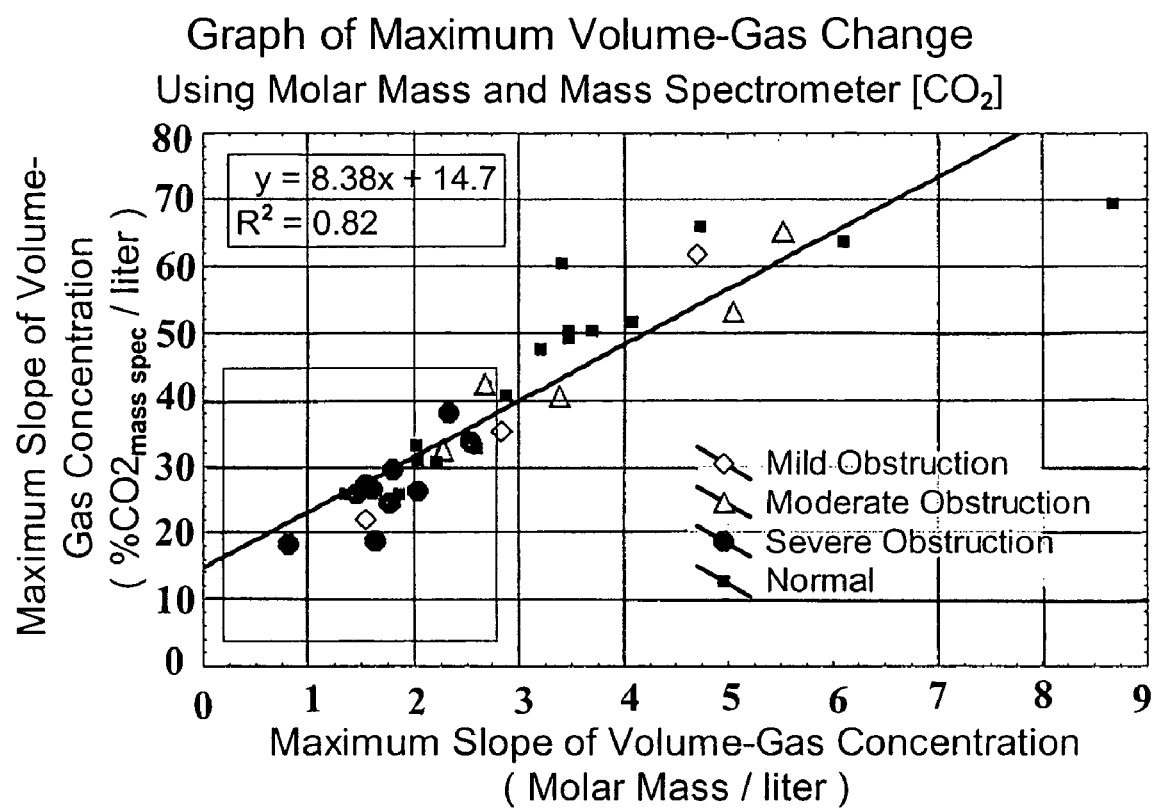
FIG. 11 illustrates a graph showing correlation of maximum slope between $CO_2$ (mass spec) and molar mass according to an embodiment of the present invention.

FIG. 11 illustrates a graph showing correlation of maximum slope between $CO_2$ (mass spec) and molar mass, which show quite similar slope for both $CO_2$ and molar mass having correlation factor value, $r^2$=0.8233.

Molar mass measurements are simple because no external sensors or analyzers are needed and no calibration is necessary. They also correlate well with traditional measures of $CO_2$. Therefore, molar mass measurements can provide an effort-independent test that will diagnose the presence of and degree of airway obstruction. Molar mass data may add additional information to traditional spirometry from the shape of the molar mass vs. volume curves.

While the invention has been shown and described with reference to a certain preferred embodiment thereof, it will be understood by those skilled in the art that various changes in form and details may be made therein without departing from the spirit and scope of the invention.

What is claimed is:

1. Device for lung function diagnosis without cooperation of a patient, comprising
    an ultrasonic gas flow and molar mass sensor based upon a transit-time or time-of-flight method,
    an exchangeable or fixed flow tube having a mouthpiece,
    software used for tidal breathing analysis of a patient without cooperation of the patient by measuring flow, volume and molar mass, using a statistical method for analysis of said measured signals and subsequently deriving from results of the analysis a lung function status index for diagnostic or monitoring purposes, and
    instructions provided on a computer-readable medium, structured and arranged to perform the analysis based on a single deep exhalation or a combination of quiet breathing and a single deep exhalation, by the patient,
    wherein the derived lung function status index is structured and arranged to be used for the diagnosis or prediction of COPD (chronic obstructive pulmonary disease) or asthma.

2. Device according to claim 1, structured and arranged to perform the statistical analysis using at least one of
    (i) a molar mass over volume graph,
    (ii) molar mass over time graph,
    (iii) parameters directly derived from flow,
    (iv) anthropometric data from the patient such as gender, ethnicity, height, age, weight etc., and
    (v) data from a questionnaire answered by the patient.

3. Device according to claim 2, structured and arranged to use native molar mass, assuming a fixed temperature for the molar mass computation, or normal molar mass by using a temperature model, one or several temperature measurements or a combination of both for computing temperature along the sound transmission path.

4. Device according to claim 3, structured and arranged to base the statistical analysis on a single or several breaths of tidal breathing where during several breaths, data of the several breaths is overlaid to construct an averaged curve.

5. Device according to claim 4, structured and arranged to be used for trending of lung function status in a patient.

6. Device according to claim 5, wherein the statistical analysis uses "fuzzy class" prediction.

7. Device according to claim 6, structured and arranged to be used for screening a population for lung function abnormalities.

8. Method for lung function diagnosis without cooperation of a patient, comprising the steps of
   using a device including an ultrasonic gas flow and molar mass sensor based on a transit-time or time-of-flight method, an exchangeable or fixed flow tube with a mouthpiece, appropriate software used for tidal breathing analysis of a patient without cooperation of a patient and instructions provided on a computer-readable medium,
   measuring flow, volume and molar mass,
   using statistical method for analysis of said measured signals,
   subsequently deriving from results of the analysis, a lung function status index for diagnostic or monitoring purposes,
   basing on a single deep exhalation or a combination of quiet breathing and a single deep exhalation, and
   using the lung function status index for the diagnosis or prediction of COPD (chronic obstructive pulmonary disease) or asthma.

9. Method according to claim 8, comprising the step of performing the statistical analysis using at least one of
   (i) a molar mass over volume graph,
   (ii) a molar mass over time graph,
   (iii) parameters directly derived from flow,
   (iv) anthropometric data from the patient such as gender, ethnicity, height, age, weight etc., and
   (v) data from a questionnaire answered by the patient.

10. Method according to claim 9, comprising the step of using native molar mass, where a fixed temperature is assumed for the molar mass computation, or normal molar mass by the step of using a temperature model, one or several temperature measurements or a combination of both for computing temperature along the sound transmission path.

11. Method according to claim 10, comprising the step of basing the statistical analysis on a single or several breaths of tidal breathing, where in the case of several breaths data of said several breaths is overlaid to construct an averaged curve.

12. Method according to claim 11, comprising the step of trending lung function status in a patient.

13. Method according to claim 12, wherein the statistical analysis uses "fuzzy class" prediction.

14. Method according to claim 13, comprising the step of screening a population for lung function abnormalities.

* * * * *